United States Patent [19]

Jenkins

[11] 4,418,215

[45] Nov. 29, 1983

[54] CATALYSTS

[75] Inventor: John W. Jenkins, Chalkhouse Green, Near Reading, England

[73] Assignee: Johnson, Matthey & Co., Limited, London, England

[21] Appl. No.: 320,065

[22] Filed: Nov. 10, 1981

Related U.S. Application Data

[62] Division of Ser. No. 214,983, Dec. 10, 1980.

[30] Foreign Application Priority Data

Dec. 18, 1979 [GB] United Kingdom ............... 7943484

[51] Int. Cl.$^3$ .......................................... C07C 47/052
[52] U.S. Cl. .................................... 568/473; 568/472
[58] Field of Search ............................... 568/472, 473

[56] References Cited

U.S. PATENT DOCUMENTS

| 4,167,527 | 9/1979 | Nielsen | 568/473 |
| 4,208,353 | 6/1980 | Webster et al. | 568/473 |
| 4,219,509 | 8/1980 | Nielsen et al. | 568/473 |
| 4,306,089 | 12/1981 | Webster et al. | 568/473 |
| 4,330,437 | 5/1982 | Kruager | 568/473 |

OTHER PUBLICATIONS

Masumoto et al., "Journal of Catalysis", vol. 68, pp. 355–361, (1981).

Primary Examiner—Werren B. Lone
Attorney, Agent, or Firm—Cushman, Darby & Cushman

[57] ABSTRACT

This invention is concerned with catalysis. More especially, the invention relates to catalytic metal or alloy or both in a form having enhanced catalytic properties, and to the use thereof in catalytic processes. In more detail a catalyst or catalyst substrate according to the invention comprises at least one metal and/or alloy body made by a melt spun or a melt extraction process.

2 Claims, No Drawings

CATALYSTS

This is a division of application Ser. No. 214,983, filed Dec. 10, 1980.

This invention is concerned with catalysis. More especially, the invention relates to catalytic metal or alloy or both in a form having enhanced catalytic properties, and to the use thereof in catalytic processes.

Catalytic processes involving the use of catalytic metal or alloy are employed, inter alia, for the oxidation and dehydrogenation of methanol in the manufacture of formaldehyde, for the oxidation of ammonia in the manufacture of nitric acid and for the dehydrogenation of isopropanol.

One well known catalytic process for the manufacture of formaldehyde from methanol comprises passing a pre-heated mixture of air and up to 50 vol % methanol vapor through a catalytic bed of crystalline silver powder maintained at temperatures between 450° C. and 650° C. and preferably at a temperature of about 635° C. Under these conditions the following dehydrogenation and oxidation reactions are believed to take place simultaneously:

$$CH_3OH \rightarrow HCOH + H_2 - 2 \text{ 0Kcal} \quad (i)$$

$$CH_3OH + \tfrac{1}{2}O_2 \rightarrow HCOH + H_2O + 38 \text{ Kcal} \quad (ii)$$

although reaction (i) may predominate.

The product gases are fed to a series of countercurrent scrubbers which cool the gases and yield solutions of unreacted methanol and formaldehyde from which formaldehyde is obtained by fractionation. Conversion rates range from 60–73% with nett yields of from 83–92%.

Although crystalline silver powder is a fairly effective catalyst for this process, it has the disadvantages that it is relatively difficult to make and to handle and that it has a relatively short in-service life. This is due to the fact that under the conditions which obtain in the catalyst bed, the silver powder undergoes extensive sintering and dendritic growth. As a result, "plugs" are formed in the bed leading to flow maldistribution and excessive pressure drops.

For the oxidation of ammonia in the manufacture of nitric acid, a mixture of ammonia and air is passed through an assembly of closely woven gauzes made from platinum or platinum-base alloy wire. A typical alloy used for this purpose is 10% rhodium-platinum alloy. The fabrication of these gauzes is both tedious and time consuming because it involves drawing platinum or platinum alloy ingots down to fine wire with many intermediate annealing stages followed by the technically difficult and costly process of weaving the resulting wire into gauzes. The result is that the gauzes are highly expensive.

For the catalytic dehydrogenation is isopropanol, fused lumps of brass spelter are used as the catalyst and the production of these is a relatively tedious, time consuming and therefore expensive process.

The present invention provides metal and/or alloy catalysts which may be used, inter alia, for the catalytic processes just referred to and which are cheaper to make, in some cases very significantly so, than those catalysts at present employed. Catalysts according to the present invention mitigate or overcome some, if not all, of the disadvantages associated with at least those processes just described. Further these catalysts are frequently catalytically more effective than those they may replace.

The invention is based upon the surprising realisation that catalytic metal and alloy bodies made by the melt spin process (which bodies are accordingly often referred to as "melt spun" bodies) or metal or alloy bodies made by the melt extraction process (this being sometimes referred to as the "melt drag" process) have, in general, enhanced catalytic properties when compared with such bodies made by other methods.

In the melt spin process, a stream of molten metal or alloy is either allowed to solidify in free flight or is caused to solidify by contact with a so-called "chill-block" which is cooled or possesses high thermal capacity or both and is generally in the form of a rotating wheel, disc or dish or a moving belt. The stream of molten metal impinges on the body and is thrown off or removed therefrom as a continuous or discontinuous filament depending upon such parameters as the temperature and speed of the stream of molten metal or alloy as it impinges on the chill block and the surface speed of the chill block at the point of impingement. For example, if the temperature of the impinging stream and the surface speed of the chill block are held constant, any increase in the speed of impingement of the stream on the chill block will tend to cause the metal or alloy to pile up on the block so that the filament leaving it will increase in thickness.

On the other hand, if the speed of impingement is progressively reduced, the tendency of the metal or alloy to pile up and the thickness of the resulting filament is also progressively reduced until the point is reached where the thinnest continuous filament possible at the particular temperature of the metal or alloy will be produced. Any further reduction in the speed of impingement will then result in the production of discontinuous filaments. Methods of making melt spun bodies are disclosed in U.S. Pat. Nos. 2,825,108, 2,879,566, 2,886,866 and 2,976,590.

In the melt extraction or melt-drag process, molten metal or alloy first forms a meniscus between a nozzle at the end of a feed tube from a crucible containing a static head of the molten metal or alloy and the curved surface of a cooled rotating body such as a drum. The meniscus is partially solidified by contact with the body surface which drags away the solidifying metal or alloy to form a continuous filament. Solidification is completed as the body rotates and the solidified filament, which may be in the form of a wire or strip, is removed from the body surface before it has executed a complete revolution and is then coiled.

A metal and/or alloy body or bodies made at least in part, by melt spin or melt extraction processes will, throughout the remainder of this specification and whenever the context permits, be referred to as "a body" or "bodies" of the type herein described. Associated with this will be an indication as to whether each body is made of metal or alloy or both.

As previously indicated, we have now discovered, to our surprise, that catalytic metal and alloy bodies of the type herein described have enhanced catalytic properties as compared with such bodies made by other processes. This, we believe, may be due to the surface configurations of these bodies which, in turn, stems at least in part from the particular crystalline structures achieved by the melt spin and melt extraction processes. By "catalytic metal and alloy" bodies here and elsewhere in this specification is meant metal and alloy bodies which are inherently catalytic or which have been rendered catalytic or more catalytic by, for example, the application to their surfaces, after or during fabrication of one or more continuous or discontinuous layers of catalytic material.

According to a first feature of the present invention, therefore, a catalyst comprises one or more catalytic metal and/or alloy bodies of the type herein described.

Suitable forms of the body or bodies in a catalyst according to this first feature of the invention comprise those set forth below, although the list is by no means exhaustive.

(1) Each body may be of, or may comprise, one or more elongate wires or strips wound-up upon itself or themselves in a random fashion to form one or more relatively porous "scouring pad"-like structures. In such structures, the wire or strip may be crimped and/or otherwise deformed so as to increase the area of metal or alloy exposed to any fluid (vapour, gas or liquid) passing through the structures.

(2) Each body may be elongate, but relatively short in length and may be crimped and/or otherwise deformed in order that an agglomeration, cluster or assemblage of them will have many interstices so that firstly, a fluid may pass therethrough with only a small pressure drop and secondly, so that a relatively large area of the metal or alloy will be exposed to such a fluid during its passage through the agglomeration, cluster or assemblage.

The present invention therefore provides a catalyst or a catalyst substrate comprising at least one metal and/or alloy body made by a melt spun or a melt extraction process. Each body may be made from silver or an alloy comprising silver and at least one of the metals platinum, rhodium, ruthenium, palladium, iridium, gold and copper or an alloy of platinum and gold.

Preferably, each body comprises 0.1 to 0.5 wt % of at least one of the metals platinum, rhodium, ruthenium, palladium, iridium and gold, balance silver, or 0.1 to 20 wt % copper balance silver.

One way of preparing a body of the type just described is to pass a melt spun or melt extracted ribbon of catalytic metal or alloy between the meshing teeth of crimping rollers and then to cut the so-crimped ribbon into short pieces, say 0.5 cm in length. In this way a particulate catalytic packing is formed which may be poured into a reactor vessel to form a high porosity, relatively uniformly packed bed of catalyst.

Such a packing, agglomeration, cluster or assemblage may be located between retaining gauzes and/or other reticulate or foraminous bodies, the said gauzes and/or bodies being catalytically inert or otherwise. Arrangements of this type are disclosed in our co-pending application No. 7936209.

An alternative way of preparing the short lengths of metal or alloy which form the "particulate" packing is simply to adjust the operating conditions of the melt spin process so that a discontinuous product in the form of "flakes" of metal or alloy is obtained. In this case, however, it is more difficult to crimp and/or otherwise deform the metal or alloy than when a long length is first treated and then cut up into pieces.

Further, the catalytic packing located between retaining gauzes and/or other reticulate or formaminous bodies may be one or more "scouring pad"-like bodies of the type disclosed in the foregoing section 1 or it may comprise such a body or bodies together with "particulate" catalyst material of type disclosed in Section 2.

Further, any arrangements of the types disclosed in the foregoing Sections 1 and 2 may comprise mixtures of catalytic metal and alloy bodies of the type herein described.

In addition to catalysts according to a first feature of this invention, the invention also includes catalytic processes when carried out with the use of such catalysts.

One such process involves the production of formaldehyde from methanol and oxygen and, for this purpose, the catalyst employed is a copper silver alloy body, or a plurality of such bodies of the type herein described. The copper content of the alloy may range from 0.1 to 20 wt. % but is preferably not more than 7.5 wt%.

A way in which such a process for the manufacture of formaldehyde has been carried out will now be described by way of example only.

Silver/copper alloys containing 7.5 wt % and 16 wt % of copper respectively were melted in a quartz tube surrounded by the coil of an electrical induction furnace. Argon gas was introduced under pressure into the space above the molten alloy in the tube so as to drive out the alloy through a small hole in the bottom of the tube onto the surface of a rapidly spinning, water-cooled copper wheel.

The resulting rapidly quenched alloy was formed as a continuous tape, filament or ribbon 1–2 mm wide and 50–60 microns thick at a linear rate of 15 m/sec. This ribbon was then passed through the meshing teeth of crimping rollers with the result that in profile it resembled a square wave with a period of 2 mm and an amplitude of 1 mm. The crimped tape was then cut into lengths of about 1 cm to yield a particulate metal suitable for loading into a fixed bed catalytic reactor. The use of crimped lengths of metal in this way provides an alloy catalyst bed having a very low pressure drop and a very high surface area.

The conversion of methanol to formaldehyde is usually carried out under conditions which avoid the hazardous explosive composition range. That is to say, it is carried out either below the lean flammability limit or above the rich flammability limit. Experiments under methanol lean conditions led to the complete oxidation of the methanol but by operating with methanol rich $O_2$/methanol mixtures, dehydrogenation and selective oxidation to formaldehyde was achieved.

The apparatus used consisted of a bubbler containing anhydrous methanol through which was passed premixed 8% oxygen in helium at a controlled flow rate of 30 ml/mixture. The resulting methanol saturated gas (the saturation vapour pressure of methanol is 120 mm Hg at 25° C.) was then passed to the top of a silica tube of 0.5 cm internal diameter and containing 1 gm of the particulate alloy catalyst. The silica tube was mounted vertically inside a closely fitting machined brass block which was, in turn, located within an electrically heated tubular furnace. The effluent from this gaseous reactor was condensed in a trap partially immersed in liquid nitrogen. The water, formaldehyde and unconverted methanol together with other condensible products in the effluent were collected and subsequently analysed by gas chromatography.

This analysis was performed using 1.5 feet of ¼ inch stainless steel tubing packed with "Carbosieve B," a commercially available carbon molecular sieve, held at 150° C.

In more detail, when carrying out the experiment, one gram of the particulate alloy catalyst was placed in the centre of the silica furnace tube and heated to 650° C. in the stream of 8% $O_2$He in helium and preconditioned for at least 30 minutes. After preconditioning, the reactor was cooled to the desired run temperature allowed to stabilise at that temperature whilst methanol-vapour charged 8% $O_2$He was passed through it, whereafter the products were collected for a further 30 minutes and then analysed.

The experimental procedure just described was carried out at temperatures of 250° C., 300° C., 400° C., 500° C. and 600° C. using 7.5 wt % Cu/Ag and 16 wt % Cu/Ag catalysts. Finally, the procedure was repeated at these temperatures but with the 1 gram of Cu/Ag catalyst in the silica tube replaced by 1 gram of a catalyst consisting of 12-16 mesh silver crystals to provide control results. In all this work, the molar ratio of oxygen to methanol vapour was about 0.5 and the 'weight hourly space velocity' of the methanol vapour (the weight of methanol vapour per unit weight of catalyst passing through the reactor per hour) was about 0.36.

The respective percentages of methanol and formaldehyde in the effluent from the reactor in each test are given in the attached Table 1. From this it is evident that the melt spun 7.5 wt % Cu/Ag alloy is, in general, catalytically more effective than the silver crystals that are conventionally used for the conversion of methanol vapour to formaldehyde. This 7.5 wt % Cu/Ag alloy catalyst according to this invention also has the advantage that it is easier to make and handle than the conventional catalyst and, furthermore, can be used to provide a catalyst bed which permits the ready passage of gas through it and is not prone to blockages and flow maldistribution.

Although only detailed results for 7.5 wt % Cu/Ag and 16 wt % Cu/Ag alloys are given here, we believe that one or more alloy compositions which will provide catalysts with optimum selectivity in promoting the formation of formaldehyde from methanol so that they at the same time minimise the formation of carbon monoxide and carbon dioxide, lie within the range 3-4 wt % Cu/Ag.

Although only one example of the use of a catalyst according to the invention has been given here, such catalysts are capable of many more applications. Included among these are the oxidation of ammonia gas in the manufacture of nitric acid, as will be evident from our corresponding Application No. 7936209; the removal of unwanted components from the exhaust gases of internal combustion engines and from certain industrial effluent gases and vapours and certain selective oxidation reactions such as the oxidation of propylene to acrolein and of butene to methacrolein.

A catalyst for the removal, for example, of unwanted components such as hydrocarbons, carbon monoxide and oxides of nitrogen (NOx) from the exhaust gases of internal combustion engines is conveniently in the form of metal and/or alloy bodies of the type herein described which are relatively short in length and crimped and/or otherwise deformed in order to present a relatively large surface area of the gases. Such bodies are described in Section 2 above. The resulting particulate catalyst may be used to fill a reaction chamber in, for example, the exhaust system of a motor vehicle and will provide a relatively inexpensive catalytic bed having a large contact area, low pressure drop and good flow characteristics. In this way it has many advantages over the catalyst-coated ceramic and metal 'honeycomb' monoliths that are commonly employed for the purpose of cleaning up motor vehicle exhaust gases.

In the following, test results are included using spun melt alloys according to the invention as catalysts as compared with the use of known silver crystals in the production of formaldehyde from methanol. In each case the tests were carried out over two consecutive days at hourly space velocities of $8 \times 10^4$ using 20 mole % of water in the feed stream.

| | | % by weight Product analysis | | |
|---|---|---|---|---|
| | Mole % $CH_3OH$ | $CH_3OH$ | HCHO | $CO_2$ |
| Ag Crystal (Prior art - for comparison) | | | | |
| Day 1 | 48 | 39.8 | 56.7 | 3.5 |
| | 40 | 12.5 | 78.7 | 8.8 |
| | 38 | 5.8 | 87.3 | 6.9 |
| Day 2 | 52 | 42.1 | 35.5 | 22.4 |
| | 48 | 19.2 | 39.5 | 41.3 |
| | 44 | 27.4 | 41.8 | 30.8 |
| | 42 | 18.9 | 40.3 | 40.8 |
| | 40 | 12.8 | 43.0 | 44.2 |
| | 38 | 10.3 | 42.4 | 47.3 |
| Melt Spun Silver (According to the invention) | | | | |
| Day 1 | 52 | 35.3 | 54.7 | 10.0 |
| | 48 | 27.3 | 60.4 | 12.3 |
| | 44 | 15.4 | 70.2 | 14.4 |
| Day 2 | 52 | 39.7 | 53.8 | 6.5 |
| | 48 | 24.7 | 67.3 | 8.0 |
| | 44 | 17.9 | 72.2 | 9.9 |
| | 40 | 11.4 | 75.1 | 13.5 |
| Melt Spun 0.5% Au/Ag (According to the invention) | | | | |
| Day 1 | 50 | 39.6 | 56.2 | 4.2 |
| | 48 | 34.4 | 59.7 | 5.9 |
| | 46 | 31.9 | 61.3 | 6.8 |
| | 44 | 23.2 | 66.6 | 10.2 |
| | 42 | 28.4 | 63.2 | 8.4 |
| Day 2 | 48 | 35.3 | 60.0 | 4.7 |
| | 46 | 30.4 | 63.2 | 6.4 |
| | 44 | 21.4 | 70.1 | 8.5 |
| | 42 | 18.4 | 73.6 | 8.0 |
| Melt Spun 0.1% Pt/Ag (According to the invention) | | | | |
| Day 1 | 50 | 42.3 | 52.7 | 5.0 |
| | 48 | 37.5 | 56.7 | 5.8 |
| | 46 | 34.3 | 59.7 | 6.0 |
| | 44 | 29.0 | 62.7 | 8.3 |
| | 42 | 23.8 | 69.4 | 6.8 |
| Day 2 | 50 | 49.5 | 44.3 | 6.2 |
| | 48 | 44.5 | 48.3 | 7.2 |
| | 46 | 39.0 | 52.1 | 8.9 |
| | 44 | 34.3 | 53.9 | 11.8 |
| | 42 | 28.7 | 59.7 | 11.6 |

When catalyst bed removed a hole was found to have been burnt therethrough which may have affected results on Day 2.

TABLE 1

| | Analysis of Reactor Effluent | | | | | | | | | |
|---|---|---|---|---|---|---|---|---|---|---|
| | Reactor Temperature °C. | | | | | | | | | |
| | 250 | | 300 | | 400 | | 500 | | 600 | |
| Catalyst | % CH$_3$OH | % HCOH | % CH$_3$OH | % HCOH | % CH$_3$OH | % HCOH | % CH$_3$OH | % HCOH | % CH$_3$OH | % HCOH |
| Silver Crystal 12–16 mesh | 81 | 0 | 56 | 0 | 30 | 20 | 30 | 40 | 19 | 40 |
| Melt Spun 7.5% Cu/Ag alloy | 91 | 0 | 71 | 0 | 20 | 15 | 8 | 50 | 3 | 50 |
| Melt Spun 16% Cu/Ag alloy | 91 | 0 | 66 | 0 | 41 | 20 | 24 | 40 | 9 | 40 |

I claim:

1. A process for the oxidative dehydrogenation of methanol to produce formaldehyde which comprises contacting a mixture of methanol and oxygen in which the ratio of methanol to oxygen is above the rich flammability limit with a catalyst or catalyst substrate comprising a metal body wherein said body comprises a silver alloy containing silver and from 0.1 to 7.5% by weight of copper and is made by a melt spin or melt extraction process, said body being in the form of an elongate element.

2. A process as claimed in claim 1 wherein the alloy comprises from 3 to 4% by weight of copper.

* * * * *